United States Patent
Bugdahn et al.

(10) Patent No.: US 12,215,076 B2
(45) Date of Patent: *Feb. 4, 2025

(54) METHOD FOR PRODUCING LIMONENE AND COMPOSITION CONTAINING LIMONENE

(71) Applicant: SYMRISE AG, Holzminden (DE)

(72) Inventors: Nikolas Bugdahn, Holzminden (DE); Diego Jaime, Holzminden (DE); Bernhard Rußbüldt, Höxter (DE); Frank Strüver, Hameln (DE)

(73) Assignee: Symrise AG, Holzminden (DE)

( * ) Notice: Subject to any disclaimer, the term of this patent is extended or adjusted under 35 U.S.C. 154(b) by 0 days.

This patent is subject to a terminal disclaimer.

(21) Appl. No.: 17/800,089

(22) PCT Filed: Feb. 18, 2020

(86) PCT No.: PCT/EP2020/054230
§ 371 (c)(1),
(2) Date: Aug. 16, 2022

(87) PCT Pub. No.: WO2021/164850
PCT Pub. Date: Aug. 26, 2021

(65) Prior Publication Data
US 2023/0167041 A1  Jun. 1, 2023

(51) Int. Cl.
C07C 5/31  (2006.01)
B01J 29/70  (2006.01)

(52) U.S. Cl.
CPC ............ *C07C 5/31* (2013.01); *B01J 29/7038* (2013.01); *C07C 2529/06* (2013.01); *C07C 2601/16* (2017.05)

(58) Field of Classification Search
None
See application file for complete search history.

(56) References Cited

U.S. PATENT DOCUMENTS

2004/0138051 A1* 7/2004 Shan .................. C07C 2/66
423/700

FOREIGN PATENT DOCUMENTS

WO  2011/061204 A1  5/2011

OTHER PUBLICATIONS

Ma, Xuetao et al.; "Highly selective isomerization of biomass [beta]-pinene over hierarchically acidic MCM-22 catalyst," Microporous and Mesoprous Materials, vol. 237, Sep. 23, 2016, pp. 180-188.

* cited by examiner

*Primary Examiner* — Thuan D Dang
(74) *Attorney, Agent, or Firm* — Dilworth & Barrese, LLP

(57) ABSTRACT

The invention relates to a method for producing limonene comprising or consisting of the following steps: (a) providing beta-pinene or a beta-pinene containing starting material: (b) admixing the starting material with a catalytically effective amount of a MWW-type zeolite: (C) heating the reaction mixture to a temperature in the range of between 60 and 100° C.; and optionally (d) separating the limonene or a limonene-enriched fraction from the sump.

9 Claims, 1 Drawing Sheet

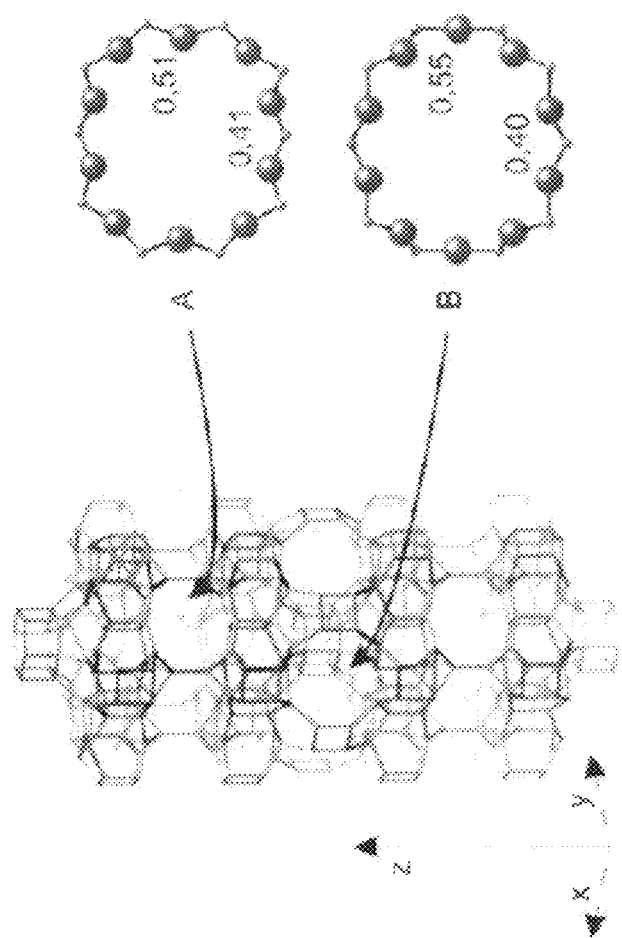

METHOD FOR PRODUCING LIMONENE AND COMPOSITION CONTAINING LIMONENE

FIELD OF THE INVENTION

The present invention is in the field of terpene compounds and relates to a process for catalytic rearrangement of beta-pinene to limonene.

TECHNOLOGICAL BACKGROUND

Limonene is a natural substance from the group of monocyclic terpenes, which occurs in two enantiomers

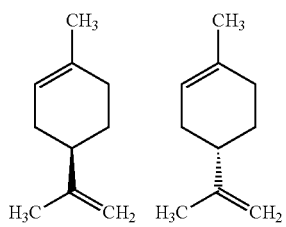

(R)-(+)-limonene (also referred to as D-(+)-limonene or (+)-limonene for short) and (S)-(−)-limonene [also referred to as L-(−)-limonene or (−)-limonene for short]. The racemate of the two enantiomers is also known as dipentene.

Limonene is the most common monoterpene found in plants. (R)-(+)-Limonene is present especially in bitter orange peel oil, caraway oil, dill oil, coriander oil, lemon oil (about 65%) and orange oil (usually >90%). It has an orange-like fragrance. By contrast, (S)-(−)-limonene is present in noble fir and peppermint oil and smells of turpentine. Racemic limonene occurs inter alia in pine oil, Siberian pine needle oil, neroli oil, nutmeg oil and camphor oil.

The biosynthesis of limonene proceeds from geranyl pyrophosphate (GPP).

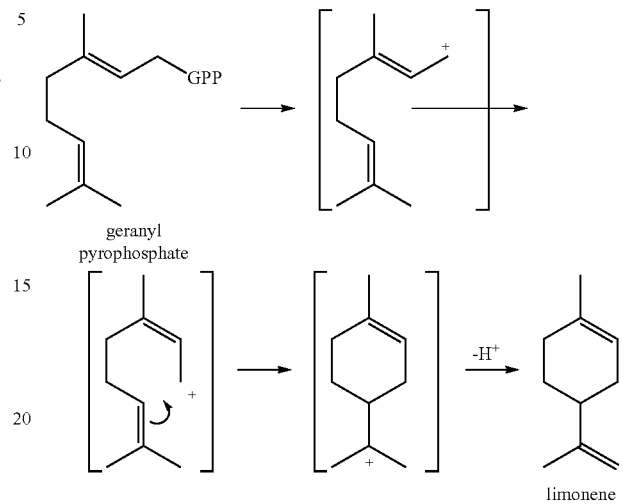

Limonene is an essential raw material for the fragrance industry and a starting material for a multiplicity of applications and products. It has in particular recently also been used as a "green" solvent and represents an alternative to the environmentally questionable BTX solvents.

While beta-pinene is a readily available source for the production of limonene, the difficulty in the acid-catalyzed isomerization of ß-pinene is the potential for forming a broad product spectrum of bi-, tri-, and monocyclic terpenes via a series of equilibrium reactions that must be avoided to achieve high limonene selectivity. A selection from this possible product range is shown below.

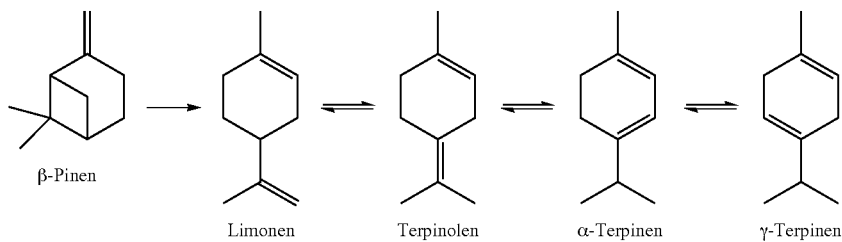

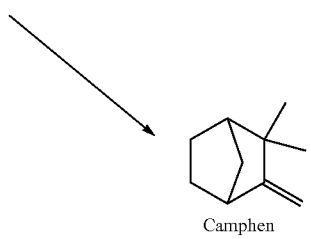

RELEVANT PRIOR ART

The first relevant publications include the two property rights U.S. Pat. No. 3,780,124 (DAVIS) and U.S. Pat. No. 3,780,125 (TAKACS) from 1973, which propose applying iodine to zeolites for the rearrangement of alpha-pinene.

U.S. Pat. No. 4,508,930 (WIDEMANN) discloses the rearrangement of terpenes into limonene in the presence of supported alkali metal sulfide catalysts at high temperatures.

The isomerization of pinene to limonene and other byproducts in the presence of zeolites is already known from U.S. Pat. No. 3,270,075 (GLIDDEN). The reaction takes place in the liquid phase at 65° C. to 110° C. The catalyst is generally described as $Me_{x/n}[(AlO_2)_x(SiO_2)_y]*zH_2O$ and specific mention is made of:

$Na_{86}[(AlO_2)_{86}(SiO_2)_{106}]*267H_2O$.

The two Dalian University Chinese patents CN 102126904B and CN 102343277B likewise describe the isomerization of pinenes to limonene in the presence of heterogeneous acid catalysts. The catalysts employed are acidic molecular sieves which have been aftertreated with halides and with bases.

Reference is also made to the two papers of Ma et. al. in MICROPOROUS AND MESOPOROUS MATERIAL 237, pp. 180-188 (2017) and Golets et al. in CHEM. REV. 115, S. 3141-3196 (2017).

The disadvantage is that the processes known from the prior art do not represent economically viable alternatives either in terms of yields or selectivities. The processes generally also operate at very high temperatures, require the use of toxic solvents, cannot be performed on a continuous basis and also exhibit insufficient catalyst service lives. In addition, the reaction products often contain unwanted byproducts such as especially terpinenes in amounts that adversely affect product quality.

OBJECT OF THE INVENTION

Due to significantly increased prices for raw materials containing limonene, there is a need to produce limonene in a simple and economically viable manner from starting materials that are significantly cheaper and available in larger quantities, specifically beta-pinene.

It is therefore a first object of the present invention to provide a process for oxidation of beta-pinene to limonene which has yields and selectivities of at least 75% and affords very largely (i.e. about 15% to 20% by weight) only camphene as a byproduct. The limonene should be obtained specifically (>90% by weight) as the L isomer.

It is a further object of the invention to run the process in such a way as to eschew the use of toxic solvents, especially from the BTX series. The reaction should also be performable on a continuous basis below 100° C. and the catalyst should have a service life that is sufficiently long to allow it to be used and recovered several times without workup.

BRIEF DESCRIPTION OF THE DRAWING

The present invention will be described in greater detail with reference to the accompanying drawing which illustrates an "MWW" zeolite type.

DESCRIPTION OF THE INVENTION

The present invention firstly provides a process for producing limonene comprising or consisting of the steps of:

(a) providing beta-pinene or a beta-pinene-containing starting material;
(b) admixing the starting material with a catalytically active amount of an MWW-type zeolite;
(c) heating the reaction mixture to a temperature in the range from about 60° C. to about 100° C. and optionally
(d) separating the limonene or a limonene-enriched fraction from the bottoms.

The rearrangement follows the reaction scheme below:

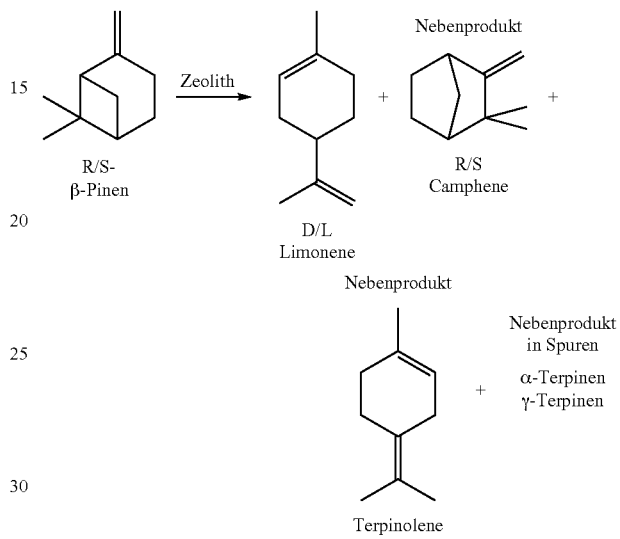

it has surprisingly been found that from the large group of zeolites known in principle for this reaction, it is precisely those of the MWW type that meet the profile of requirements specified above in every detail. The rearrangement may be carried out on a batchwise or continuous basis at temperatures of typically 70° C. to 85° C., wherein the solvent employed is selected from environmentally sound acetate esters. The catalysts have a long service life, can be reused many times without workup, and afford an almost enantiomerically pure L-limonene as the reaction product with yields and selectivities of more than 75%, preferably from 85% to 100%, in particular from 90% to 99% and very particularly preferably from 95% to 98%, wherein camphene is formed as the byproduct almost exclusively.

The invention incorporates the finding that the selectivity towards the L-isomer correlates with the purity of the beta-pinene.

It is noted that beta-pinene can exist in two enantiomeric forms, namely (S,S) and (R,R). Thus in the context of the present invention the term "beta-pinene" is to be understood as comprehending both forms or mixtures thereof. The preferred starting material is (1S, 5S) beta-pinene, also referred to as (−)-beta-pinene. Meanwhile, (1R, 5R)-beta-pinene, also referred to as (+)-beta-pinene, is particularly preferred since this allows enantiomerically pure D-limonene to be obtained.

Catalysts

The term "MWW" is understood as referring to a zeolite type as be produced in the figure (cf. pubs.acs.org/doi/abs/10.1021/jp972319k).

MWW zeolites consist of two ten-ring pore systems that are separate from one another. A distinction is made between variants A and B, where the cavities are linked linearly and sinusoidally respectively.

it is preferable to employ MWW zeolites which have previously been calcined and/or activated by acids. Particularly preferred zeolites are PSH-3 zeolites which conform to the formula $$M_{2/n}O*Al_2O_3*(20\text{-}150)SiO_2$$

and are known for example from EP0064205B1 (BAYER). Here too, it is preferable to subject the PSH-3 zeolites to calcining and/or activation by acid treatment before use. The calcining may preferably be carried out
over a period of about 1 to about 10 hours and preferably 4 to 6 hours at a temperature of about 400° C. to about 1000° C. and in particular 400° C. to 600° C., nitric acid being particularly suitable for the acid activation.

An amount of about 1% to about 5% by weight and in particular about 2% to 4% by weight of zeolite based on the amount of beta-pine may be considered an effectual catalyst amount.

Rearrangement Reaction

The reaction is preferably performed in the presence of solvents. Suitable solvents especially include esters of acetic acid and an aliphatic C1-C4-alcohol, where ethyl acetate is preferably employed.

The beta-pinene and the solvent are typically employed in a weight ratio of about 10:1 to 1:10. A weight ratio of about 2:1 to 5:1 is particularly preferred.

The reaction is preferably performed at temperatures below 150° C., preferably below 125° C. and particularly preferably below 100° C., typically at about 70° C. to about 75° C. Typical reaction times are about 1 to about 10 hours and in particular about 2 to about 5 hours.

The rearrangement reaction may be performed on a batchwise basis but in particular also on a continuous basis. The catalyst exhibits a high service life and may therefore be reused after the reaction, optionally without a preceding workup. In the batch mode it is sufficient to leave the catalyst in the bottoms and simply add fresh reactant. This makes it possible to run 10 to 15 cycles without significant reductions in conversion and selectivity. In continuous operation the service life of the catalyst is a number of weeks. The reaction mixture may optionally be admixed with a high-boiling compounds such as for example polyols, polyethers, polyesters or silicone oils.

Solvent Preparation

The present invention further provides a solvent composition obtainable or obtained by the present process, consisting of
(a) about 70 to about 80% by weight of limonene
(b) about 15% to about 20% by weight of camphene
with the proviso that the reported amounts sum to 100% by weight optionally with pinenes, terpinenes and terpinolenes.

INDUSTRIAL APPLICABILITY

The present invention finally also provides for the use of a PSH-3 zeolite, optionally after preceding calcining and/or acid activation, for rearrangement of beta-pinene into limonene, preferably in a process as elucidated above.

EXAMPLES

Example 1

Rearrangement of Beta-Pinene to Limonene with Fresh Catalyst 100 g (0.734) of a commercially available beta-pinene were initially charged in a 500 ml three-necked flask fitted with a stirrer, reflux condenser and distillation bridge and admixed with 25 g of ethyl acetate. 2 g (corresponding to 2% by weight based on beta-pinene) of PSH-3 zeolite (calcined at 550° C. for 5 hours) were then added. The mixture was heated to 70° C. with stirring and samples were taken and analyzed after 1.5 and 2 hours. After a reaction time of 2 h the reaction mixture was distilled overhead and likewise analyzed by gas chromatography. The results are reported in table 1.

TABLE 1

| Composition of bottoms and distillate (GC %) | | | |
|---|---|---|---|
| Components | Bottoms (after 1.5 h) | Bottoms (after 2 h) | Distillate (after 2 h) |
| α-Pinene | 1.65 | 1.26 | 0.98 |
| Camphene | 17.57 | 17.17 | 16.86 |
| β-Pinene | 0.09 | 0.15 | 0.22 |
| Limonene* | 761.05 | 70.26 | 73.83 |
| α-Terpinene | 1.18 | 1.50 | 1.75 |
| γ-Terpinene | 1.00 | 1.07 | 1.11 |
| Terpinolene | 2.96 | 70.37 | 3.16 |
| Selectivity (%) | 71.11 | 70.37 | 73.99 |

*>90% L-limonene

Example 2

Rearrangement of Beta-Pinene to Limonene with Recycled Catalyst

Example 1 was repeated with the exception that, after separation of the distillate, the catalyst was mixed with fresh reactant a total of 9 more times and the 10th cycle of the reaction was performed at 85° C. The composition of the bottoms of the 10th cycle was analyzed after 5, 8, 9 and 10 hours of reaction time, as was the composition of the distillate obtained after the 10th pass. The results are summarized in Table 2:

TABLE 2

| Composition of bottoms and distillate (GC %) | | | | | |
|---|---|---|---|---|---|
| Components | Bottoms (after 5 h) | Bottoms (after 8 h) | Bottoms (after 9 h) | Bottoms (after 10 h) | Distillate (after 10 h) |
| α-Pinene | 1.11 | 1.23 | 1.32 | 1.36 | 1.51 |
| Camphene | 12.92 | 14.56 | 15.31 | 15.73 | 17.64 |
| β-Pinene | 17.45 | 4.36 | 2.55 | 1.40 | 1.32 |
| Limonene* | 58.65 | 68.80 | 69.72 | 71.09 | 77.31 |
| α-Terpinene | 0.15 | 0.20 | 0.22 | 0.28 | 0.26 |
| γ-Terpinene | 0.19 | 0.24 | 0.25 | 0.26 | 0.27 |
| Terpinolene | 0.39 | 0.50 | 0.52 | 0.55 | 0.54 |
| Selectivity (%) | 71.05 | 71.94 | 71.54 | 72.10 | 78.34 |

*>90% L-limonene

Example 3

Continuous Process

From a reservoir vessel comprising beta-limonene/ethyl acetate (4:1 weight ratio) reactant was continuously conveyed using an HPLC pump into a tubular reactor which was filled with 5 g of the catalyst from example 1 and temperature-controlled to about 85° C. using an oil bath. At a flow rate of about 1 ml/min, a reaction product comprising about 77% by weight of limonene at a selectivity of about 78% was obtained.

The invention claimed is:

1. A process for producing limonene from beta-pinene, comprising the steps of:
   (a) providing beta-pinene or a beta-pinene-containing starting material;
   (b) admixing the starting material with a catalytically active amount of a PSH-3 zeolite to form a reaction mixture;
   (c) heating the reaction mixture to a temperature in the range from about 60° C. to about 100° C. in the presence of a solvent which is an ester of acetic acid and aliphatic C1-C4 alcohol to convert beta-pinene to a product containing limonene; and
   (d) separating the limonene or a limonene-enriched fraction from the product containing limonene.

2. The process as claimed in claim 1, wherein a PSH-3 zeolite which has previously been calcined and/or activated by acids is employed.

3. The process as claimed in claim 2, wherein a PSH-3 zeolite which has previously been calcined at a temperature of about 400° C. to about 1000° C. over a period of about 1 to 10 hours is employed.

4. The process as claimed in claim 2, wherein a PSH-3 zeolite which has been previously activated with nitric acid is employed.

5. The process as claimed in claim 1, wherein the catalyst is employed in an amount of about 1% to about 5% by weight based on the amount of beta-pinene.

6. The process as claimed in claim 1, wherein the beta-pinene and the solvent are employed in a weight ratio of about 10:1 to 1:10.

7. The process as claimed in claim 1, wherein the reaction is performed over a period of about 1 to about 10 hours.

8. The process as claimed in claim 1, wherein the catalyst is reused after the reaction, optionally without a preceding workup.

9. The process as claimed in claim 1, wherein the process is performed batchwise or continuously.

* * * * *